US008540727B2

United States Patent
Dishler et al.

(10) Patent No.: US 8,540,727 B2
(45) Date of Patent: Sep. 24, 2013

(54) INSERTION SYSTEM FOR CORNEAL IMPLANTS

(75) Inventors: Jon Dishler, Cherry Hills Village, CO (US); Ned Schneider, Aliso Viejo, CA (US); Alan Ngoc Le, Lake Forest, CA (US)

(73) Assignee: ReVision Optics, Inc., Lake Forest, CA (US)

( * ) Notice: Subject to any disclaimer, the term of this patent is extended or adjusted under 35 U.S.C. 154(b) by 20 days.

(21) Appl. No.: 13/411,425

(22) Filed: Mar. 2, 2012

(65) Prior Publication Data

US 2012/0165823 A1 Jun. 28, 2012

Related U.S. Application Data

(63) Continuation of application No. 11/692,835, filed on Mar. 28, 2007, now Pat. No. 8,162,953.

(51) Int. Cl.
*A61F 9/00* (2006.01)

(52) U.S. Cl.
USPC ........................................................ 606/107

(58) Field of Classification Search
USPC .................. 604/294; 606/107, 166; 623/4.1, 623/5.11, 5.14, 6.11–6.13
See application file for complete search history.

(56) References Cited

U.S. PATENT DOCUMENTS

| 2,714,721 A | 8/1955 | Stone, Jr. |
| 3,091,328 A | 5/1963 | Leonardos |
| 3,168,100 A | 2/1965 | Rich |
| 3,343,657 A | 9/1967 | Speshyock |
| 3,379,200 A | 4/1968 | Pennell |
| 3,482,906 A | 12/1969 | Volk |
| 3,743,337 A | 7/1973 | Crary |
| 3,770,113 A | 11/1973 | Thomas |
| 3,879,076 A | 4/1975 | Barnett |
| 3,950,315 A | 4/1976 | Cleaver |

(Continued)

FOREIGN PATENT DOCUMENTS

| DE | 3208729 A1 | 9/1983 |
| EP | 0308077 A2 | 3/1989 |

(Continued)

OTHER PUBLICATIONS

Schneider et al.; U.S. Appl. No. 13/549,007 entitled "Corneal Implant Retaining Devices and Methods of Use," filed Jul. 13, 2012.

(Continued)

*Primary Examiner* — Ryan Severson
*Assistant Examiner* — Ashley Fishback
(74) *Attorney, Agent, or Firm* — Shay Glenn LLP

(57) ABSTRACT

Provided therein are apparatuses, systems and methods for storing and retrieving a corneal implant and for delivering the corneal implant in or on the cornea. In an embodiment, an insertion system comprises an inserter for delivering a corneal implant to a desired location in or on the cornea. The inserter has a holding space at its distal end for holding a corneal implant therein. A solution may substantially fill the holding space with the corneal implant to keep the implant hydrated and to hold the implant in the holding space by the surface tension of the solution. The corneal implant may be preloaded in the holding space of the inserter and stored in a storage container filled with storage fluid, e.g., saline, until use. To deliver the corneal implant, the inserter is positioned at the desired location, and the corneal implant released from the holding space of the inserter.

10 Claims, 14 Drawing Sheets

(56) References Cited

U.S. PATENT DOCUMENTS

| | | |
|---|---|---|
| 3,996,627 A | 12/1976 | Deeg et al. |
| 4,030,480 A | 6/1977 | Meyer |
| 4,037,604 A | 7/1977 | Newkirk |
| 4,039,827 A | 8/1977 | Zdrok et al. |
| 4,065,816 A | 1/1978 | Sawyer |
| 4,071,272 A | 1/1978 | Drdlik |
| 4,093,291 A | 6/1978 | Schurgin |
| 4,136,406 A | 1/1979 | Norris |
| 4,157,718 A | 6/1979 | Baehr |
| 4,184,491 A | 1/1980 | McGannon |
| 4,194,814 A | 3/1980 | Fischer et al. |
| 4,238,524 A | 12/1980 | LaLiberte et al. |
| 4,257,521 A | 3/1981 | Poler |
| 4,268,133 A | 5/1981 | Fischer et al. |
| 4,326,306 A | 4/1982 | Poler |
| 4,357,940 A | 11/1982 | Muller |
| 4,392,569 A | 7/1983 | Shoup |
| 4,418,991 A | 12/1983 | Breger |
| 4,423,809 A | 1/1984 | Mazzocco |
| 4,428,746 A | 1/1984 | Mendez |
| 4,452,235 A | 6/1984 | Reynolds |
| 4,466,705 A | 8/1984 | Michelson |
| 4,490,860 A | 1/1985 | Rainin |
| 4,504,982 A | 3/1985 | Burk |
| 4,521,210 A | 6/1985 | Wong |
| 4,525,044 A | 6/1985 | Bauman |
| 4,545,478 A | 10/1985 | Waldman |
| 4,554,115 A | 11/1985 | Neefe |
| 4,554,918 A | 11/1985 | White |
| 4,565,198 A | 1/1986 | Koeniger |
| 4,580,882 A | 4/1986 | Nuchman et al. |
| 4,586,929 A | 5/1986 | Binder |
| 4,604,087 A | 8/1986 | Joseph |
| 4,607,617 A | 8/1986 | Choyce |
| 4,616,910 A | 10/1986 | Klein |
| 4,618,227 A | 10/1986 | Bayshore |
| 4,619,256 A | 10/1986 | Horn |
| 4,624,664 A | 11/1986 | Peluso et al. |
| 4,624,669 A | 11/1986 | Grendahl |
| 4,640,595 A | 2/1987 | Volk |
| 4,646,720 A | 3/1987 | Peyman et al. |
| 4,655,774 A | 4/1987 | Choyce |
| 4,662,370 A | 5/1987 | Hoffmann et al. |
| 4,663,358 A | 5/1987 | Hyon et al. |
| 4,671,276 A | 6/1987 | Reynolds |
| 4,676,792 A | 6/1987 | Praeger |
| 4,697,697 A | 10/1987 | Graham et al. |
| 4,702,244 A | 10/1987 | Mazzocco |
| 4,709,697 A | 12/1987 | Muller |
| 4,721,124 A | 1/1988 | Tuerkheimer et al. |
| 4,726,367 A | 2/1988 | Shoemaker |
| 4,750,901 A | 6/1988 | Molteno |
| 4,762,496 A | 8/1988 | Maloney et al. |
| 4,766,895 A | 8/1988 | Reynolds |
| 4,769,033 A | 9/1988 | Nordan |
| 4,772,283 A | 9/1988 | White |
| 4,778,462 A | 10/1988 | Grendahl |
| 4,798,609 A | 1/1989 | Grendahl |
| 4,806,382 A | 2/1989 | Goldberg et al. |
| 4,836,201 A | 6/1989 | Patton et al. |
| 4,840,175 A | 6/1989 | Peyman |
| 4,842,599 A | 6/1989 | Bronstein |
| 4,844,242 A | 7/1989 | Chen et al. |
| 4,851,003 A | 7/1989 | Lindstrom |
| 4,860,885 A | 8/1989 | Kaufman et al. |
| 4,886,488 A | 12/1989 | White |
| 4,888,016 A | 12/1989 | Langerman |
| 4,897,981 A | 2/1990 | Beck |
| 4,911,715 A | 3/1990 | Kelman |
| 4,919,130 A | 4/1990 | Stoy et al. |
| 4,923,467 A | 5/1990 | Thompson |
| 4,934,363 A | 6/1990 | Smith et al. |
| 4,936,825 A | 6/1990 | Ungerleider |
| 4,946,436 A | 8/1990 | Smith |
| 4,955,903 A | 9/1990 | Sulc et al. |
| 4,968,296 A | 11/1990 | Ritch et al. |
| 4,971,732 A | 11/1990 | Wichterle |
| 4,976,719 A | 12/1990 | Siepser |
| 5,019,084 A | 5/1991 | Aysta et al. |
| 5,019,098 A | 5/1991 | Mercier |
| 5,022,414 A | 6/1991 | Muller |
| 5,030,230 A | 7/1991 | White |
| 5,041,081 A | 8/1991 | Odrich |
| 5,063,942 A | 11/1991 | Kilmer et al. |
| 5,071,276 A | 12/1991 | Nielsen et al. |
| 5,073,163 A | 12/1991 | Lippman |
| 5,092,837 A | 3/1992 | Ritch et al. |
| 5,098,444 A | 3/1992 | Feaster |
| 5,108,428 A | 4/1992 | Capecchi et al. |
| 5,112,350 A | 5/1992 | Civerchia et al. |
| 5,123,905 A | 6/1992 | Kelman |
| 5,123,921 A | 6/1992 | Werblin et al. |
| 5,139,518 A | 8/1992 | White |
| 5,171,213 A | 12/1992 | Price, Jr. |
| 5,173,723 A | 12/1992 | Volk |
| 5,178,604 A | 1/1993 | Baerveldt et al. |
| 5,180,362 A | 1/1993 | Worst |
| 5,181,053 A | 1/1993 | Brown |
| 5,188,125 A | 2/1993 | Kilmer et al. |
| 5,190,552 A | 3/1993 | Kelman |
| 5,192,317 A | 3/1993 | Kalb |
| 5,196,026 A | 3/1993 | Barrett et al. |
| 5,211,660 A | 5/1993 | Grasso |
| 5,225,858 A | 7/1993 | Portney |
| 5,229,797 A | 7/1993 | Futhey et al. |
| 5,244,799 A | 9/1993 | Anderson |
| 5,258,042 A | 11/1993 | Mehta |
| 5,270,744 A | 12/1993 | Portney |
| 5,273,750 A | 12/1993 | Homiger et al. |
| 5,282,851 A | 2/1994 | Jacob-LaBarre |
| 5,300,020 A | 4/1994 | L'Esperance, Jr. |
| 5,300,116 A | 4/1994 | Chirila et al. |
| 5,312,413 A | 5/1994 | Eaton et al. |
| 5,318,044 A | 6/1994 | Kilmer et al. |
| 5,318,046 A | 6/1994 | Rozakis |
| 5,318,047 A | 6/1994 | Davenport et al. |
| 5,336,261 A | 8/1994 | Barrett et al. |
| 5,338,291 A | 8/1994 | Speckman et al. |
| 5,344,448 A | 9/1994 | Schneider et al. |
| 5,346,464 A | 9/1994 | Camras |
| 5,370,607 A | 12/1994 | Memmen |
| 5,372,577 A | 12/1994 | Ungerleider |
| 5,385,582 A | 1/1995 | Ommaya |
| 5,391,201 A | 2/1995 | Barrett et al. |
| 5,397,300 A | 3/1995 | Baerveldt et al. |
| 5,405,384 A | 4/1995 | Silvestrini |
| 5,428,412 A | 6/1995 | Stoyan |
| 5,433,701 A | 7/1995 | Rubinstein |
| 5,454,796 A | 10/1995 | Krupin |
| 5,458,819 A | 10/1995 | Chirila et al. |
| 5,467,149 A | 11/1995 | Morrison et al. |
| 5,474,562 A | 12/1995 | Orchowski et al. |
| 5,476,445 A | 12/1995 | Baerveldt et al. |
| 5,489,301 A | 2/1996 | Barber |
| 5,493,350 A | 2/1996 | Seidner |
| 5,502,518 A | 3/1996 | Lieberman |
| 5,512,220 A | 4/1996 | Roffman et al. |
| 5,520,631 A | 5/1996 | Nordquist et al. |
| 5,521,656 A | 5/1996 | Portney |
| 5,530,491 A | 6/1996 | Baude et al. |
| 5,533,997 A | 7/1996 | Ruiz |
| 5,570,142 A | 10/1996 | Lieberman |
| 5,591,185 A | 1/1997 | Kilmer et al. |
| 5,598,234 A | 1/1997 | Blum et al. |
| 5,616,148 A | 4/1997 | Eagles et al. |
| 5,620,450 A | 4/1997 | Eagles et al. |
| 5,628,794 A | 5/1997 | Lindstrom |
| 5,630,810 A | 5/1997 | Machat |
| 5,634,943 A | 6/1997 | Villain et al. |
| 5,643,276 A | 7/1997 | Zaleski |
| 5,657,108 A | 8/1997 | Portney |
| 5,682,223 A | 10/1997 | Menezes et al. |
| 5,684,560 A | 11/1997 | Roffman et al. |
| 5,715,031 A | 2/1998 | Roffman et al. |

| | | | | | | |
|---|---|---|---|---|---|---|
| 5,716,633 A | 2/1998 | Civerchia | | 6,264,648 B1 | 7/2001 | Peyman |
| 5,722,948 A | 3/1998 | Gross | | 6,264,670 B1 | 7/2001 | Chin |
| 5,722,971 A | 3/1998 | Peyman | | 6,264,692 B1 | 7/2001 | Woffinden et al. |
| 5,728,155 A | 3/1998 | Anello et al. | | 6,267,768 B1 | 7/2001 | Deacon et al. |
| 5,752,928 A | 5/1998 | de Roulhac et al. | | 6,271,281 B1 | 8/2001 | Liao et al. |
| 5,755,785 A | 5/1998 | Rowsey et al. | | 6,277,137 B1 | 8/2001 | Chin |
| 5,766,181 A | 6/1998 | Chambers et al. | | 6,280,449 B1 | 8/2001 | Blake |
| 5,772,667 A | 6/1998 | Blake | | 6,280,470 B1 | 8/2001 | Peyman |
| 5,779,711 A | 7/1998 | Kritzinger et al. | | 6,283,595 B1 | 9/2001 | Breger |
| 5,785,674 A | 7/1998 | Mateen | | 6,302,877 B1 | 10/2001 | Ruiz |
| 5,800,442 A | 9/1998 | Wolf et al. | | 6,325,509 B1 | 12/2001 | Hodur et al. |
| 5,800,529 A | 9/1998 | Brauker et al. | | 6,325,792 B1 | 12/2001 | Swinger et al. |
| 5,805,260 A | 9/1998 | Roffman et al. | | 6,361,560 B1 | 3/2002 | Nigam |
| 5,810,833 A | 9/1998 | Brady et al. | | 6,364,483 B1 | 4/2002 | Grossinger et al. |
| 5,817,115 A | 10/1998 | Nigam | | 6,371,960 B2 | 4/2002 | Heyman et al. |
| 5,824,086 A | 10/1998 | Silvestrini | | 6,391,230 B1 | 5/2002 | Sarbadhikari |
| 5,847,802 A | 12/1998 | Menezes et al. | | 6,398,277 B1 | 6/2002 | McDonald |
| 5,855,604 A | 1/1999 | Lee | | 6,398,789 B1 | 6/2002 | Capetan |
| 5,860,984 A | 1/1999 | Chambers et al. | | 6,428,572 B2 | 8/2002 | Nagai |
| 5,872,613 A | 2/1999 | Blum et al. | | 6,435,681 B2 | 8/2002 | Portney |
| 5,873,889 A | 2/1999 | Chin | | 6,436,092 B1 | 8/2002 | Peyman |
| 5,876,439 A | 3/1999 | Lee | | 6,447,519 B1 | 9/2002 | Brady et al. |
| 5,888,243 A | 3/1999 | Silverstrini | | 6,447,520 B1 | 9/2002 | Ott et al. |
| 5,913,898 A | 6/1999 | Feingold | | 6,458,141 B1 | 10/2002 | Peyman |
| 5,919,185 A | 7/1999 | Peyman | | 6,461,384 B1 | 10/2002 | Hoffmann et al. |
| 5,928,245 A | 7/1999 | Wolf et al. | | 6,471,708 B2 | 10/2002 | Green |
| 5,929,968 A | 7/1999 | Cotie et al. | | 6,474,814 B1 | 11/2002 | Griffin |
| 5,929,969 A | 7/1999 | Roffman | | 6,506,200 B1 | 1/2003 | Chin |
| 5,941,583 A | 8/1999 | Raimondi | | 6,511,178 B1 | 1/2003 | Roffman et al. |
| 5,944,752 A | 8/1999 | Silvestrini | | 6,527,389 B2 | 3/2003 | Portney |
| 5,945,498 A | 8/1999 | Hopken et al. | | 6,537,283 B2 | 3/2003 | Van Noy |
| 5,964,748 A | 10/1999 | Peyman | | 6,543,610 B1 | 4/2003 | Nigam |
| 5,964,776 A | 10/1999 | Peyman | | 6,544,286 B1 | 4/2003 | Perez |
| 5,968,065 A | 10/1999 | Chin | | 6,551,307 B2 | 4/2003 | Peyman |
| 5,976,150 A | 11/1999 | Copeland | | 6,554,424 B1 | 4/2003 | Miller et al. |
| 5,976,168 A | 11/1999 | Chin | | 6,554,425 B1 | 4/2003 | Roffman et al. |
| 5,980,549 A | 11/1999 | Chin | | 6,557,998 B2 | 5/2003 | Portney |
| 6,007,510 A | 12/1999 | Nigam | | 6,581,993 B2 | 6/2003 | Nigam |
| 6,010,510 A | 1/2000 | Brown et al. | | 6,582,076 B1 | 6/2003 | Roffman et al. |
| 6,024,448 A | 2/2000 | Wu et al. | | 6,589,203 B1 | 7/2003 | Mitrev |
| 6,033,395 A | 3/2000 | Peyman | | 6,589,280 B1 | 7/2003 | Koziol |
| 6,036,714 A | 3/2000 | Chin | | 6,592,591 B2 | 7/2003 | Polla et al. |
| 6,050,999 A | 4/2000 | Paraschac et al. | | 6,596,000 B2 | 7/2003 | Chan et al. |
| 6,055,990 A | 5/2000 | Thompson | | 6,605,093 B1 | 8/2003 | Blake |
| 6,066,170 A | 5/2000 | Lee | | 6,607,537 B1 | 8/2003 | Binder |
| 6,068,642 A | 5/2000 | Johnson et al. | | 6,607,556 B1 | 8/2003 | Nigam |
| 6,079,826 A | 6/2000 | Appleton et al. | | 6,623,522 B2 | 9/2003 | Nigam |
| 6,083,231 A | 7/2000 | Van Noy et al. | | 6,626,941 B2 | 9/2003 | Nigam |
| 6,086,202 A | 7/2000 | Chateau et al. | | 6,629,979 B1 | 10/2003 | Feingold et al. |
| 6,090,141 A | 7/2000 | Lindstrom | | 6,632,244 B1 | 10/2003 | Nigam |
| 6,102,946 A | 8/2000 | Nigam | | 6,645,246 B1 | 11/2003 | Weinschenk, III et al. |
| 6,110,166 A | 8/2000 | Juhasz | | 6,648,877 B1 | 11/2003 | Juhasz et al. |
| 6,120,148 A | 9/2000 | Fiala et al. | | 6,657,029 B2 | 12/2003 | Vanderbilt |
| 6,125,294 A | 9/2000 | Scholl et al. | | 6,666,887 B1 | 12/2003 | Callahan et al. |
| 6,129,733 A | 10/2000 | Brady et al. | | 6,673,112 B2 | 1/2004 | Nigam |
| 6,139,560 A | 10/2000 | Kremer | | 6,709,103 B1 | 3/2004 | Roffman et al. |
| 6,142,969 A | 11/2000 | Nigam | | 6,712,848 B1 | 3/2004 | Wolf et al. |
| 6,143,001 A | 11/2000 | Brown et al. | | 6,723,104 B2 | 4/2004 | Ott |
| 6,159,241 A | 12/2000 | Lee et al. | | 6,733,507 B2 | 5/2004 | McNicholas et al. |
| 6,171,324 B1 | 1/2001 | Cote et al. | | 6,733,526 B2 | 5/2004 | Paul et al. |
| 6,175,754 B1 | 1/2001 | Scholl et al. | | 6,808,262 B2 | 10/2004 | Chapoy et al. |
| RE37,071 E | 2/2001 | Gabrielian et al. | | 6,824,178 B2 | 11/2004 | Nigam |
| 6,183,513 B1 | 2/2001 | Guenthner et al. | | 6,849,090 B2 | 2/2005 | Nigam |
| 6,197,019 B1 | 3/2001 | Peyman | | 6,855,163 B2 | 2/2005 | Peyman |
| 6,197,057 B1 | 3/2001 | Peyman et al. | | 6,875,232 B2 | 4/2005 | Nigam |
| 6,197,058 B1 | 3/2001 | Portney | | 6,879,402 B2 | 4/2005 | Küchel |
| 6,203,538 B1 | 3/2001 | Peyman | | 6,881,197 B1 | 4/2005 | Nigam |
| 6,203,549 B1 | 3/2001 | Waldock | | 6,893,461 B2 | 5/2005 | Nigam |
| 6,203,557 B1 | 3/2001 | Chin | | 6,949,093 B1 | 9/2005 | Peyman |
| 6,206,919 B1 | 3/2001 | Lee | | 6,955,432 B2 | 10/2005 | Graham |
| 6,210,005 B1 | 4/2001 | Portney | | 7,128,351 B2 | 10/2006 | Nigam |
| 6,214,015 B1 | 4/2001 | Reich et al. | | 7,776,086 B2 | 8/2010 | Miller |
| 6,214,044 B1 | 4/2001 | Silverstrini | | 7,992,906 B2 | 8/2011 | Nigam |
| 6,217,571 B1 | 4/2001 | Peyman | | 8,057,541 B2 | 11/2011 | Dishler et al. |
| 6,221,067 B1 | 4/2001 | Peyman | | 8,162,953 B2 | 4/2012 | Dishler et al. |
| 6,228,114 B1 | 5/2001 | Lee | | 2001/0027314 A1 | 10/2001 | Peyman |
| 6,248,111 B1 | 6/2001 | Glick et al. | | 2001/0051826 A1 | 12/2001 | Bogaert et al. |
| 6,250,757 B1 | 6/2001 | Roffman et al. | | 2002/0010510 A1 | 1/2002 | Silvestrini |
| 6,251,114 B1 | 6/2001 | Farmer et al. | | 2002/0055753 A1 | 5/2002 | Silvestrini |

| | | |
|---|---|---|
| 2002/0101563 A1 | 8/2002 | Miyamura et al. |
| 2002/0103538 A1 | 8/2002 | Hughes et al. |
| 2002/0138069 A1 | 9/2002 | Peyman |
| 2003/0014042 A1 | 1/2003 | Juhasz et al. |
| 2003/0033010 A1 | 2/2003 | Hicks et al. |
| 2003/0069637 A1 | 4/2003 | Lynch et al. |
| 2003/0078487 A1 | 4/2003 | Jeffries et al. |
| 2003/0229303 A1 | 12/2003 | Haffner et al. |
| 2004/0019379 A1 | 1/2004 | Glick et al. |
| 2004/0034413 A1 | 2/2004 | Christensen |
| 2004/0054408 A1 | 3/2004 | Glick et al. |
| 2004/0073303 A1 | 4/2004 | Schanzlin et al. |
| 2005/0080484 A1 | 4/2005 | Marmo et al. |
| 2005/0080485 A1 | 4/2005 | Nigam |
| 2005/0113844 A1 | 5/2005 | Nigam |
| 2005/0119738 A1 | 6/2005 | Nigam |
| 2005/0143717 A1 | 6/2005 | Peyman |
| 2005/0178394 A1 | 8/2005 | Slade |
| 2005/0182350 A1 | 8/2005 | Nigam |
| 2005/0203494 A1 | 9/2005 | Holliday |
| 2005/0246016 A1 | 11/2005 | Miller et al. |
| 2006/0020267 A1 | 1/2006 | Marmo |
| 2006/0116762 A1 | 6/2006 | Hong et al. |
| 2006/0142780 A1 | 6/2006 | Pynson et al. |
| 2006/0142781 A1 | 6/2006 | Pynson et al. |
| 2006/0173539 A1 | 8/2006 | Shiuey |
| 2006/0235430 A1 | 10/2006 | Le et al. |
| 2007/0027538 A1 | 2/2007 | Aharoni et al. |
| 2007/0106318 A1 | 5/2007 | McDonald |
| 2007/0106376 A1 | 5/2007 | Roberts et al. |
| 2007/0129797 A1 | 6/2007 | Lang et al. |
| 2007/0255401 A1 | 11/2007 | Lang |
| 2007/0280994 A1 | 12/2007 | Cunanan |
| 2008/0262610 A1 | 10/2008 | Lang et al. |
| 2009/0198325 A1 | 8/2009 | Holliday et al. |
| 2009/0216217 A1 | 8/2009 | Odrich et al. |
| 2011/0218623 A1 | 9/2011 | Dishler et al. |
| 2011/0290681 A1 | 12/2011 | Nigam |
| 2012/0046680 A1 | 2/2012 | Dishler et al. |
| 2012/0203238 A1 | 8/2012 | Nigam |

FOREIGN PATENT DOCUMENTS

| | | |
|---|---|---|
| EP | 0420549 A2 | 4/1991 |
| EP | 0729323 B1 | 7/1998 |
| EP | 0668061 B1 | 9/2000 |
| JP | 01-195853 | 8/1989 |
| JP | 02-211119 | 8/1990 |
| JP | 5502811 | 5/1993 |
| JP | H06510687 | 12/1994 |
| JP | 08-501009 | 2/1996 |
| JP | 9-504706 | 5/1997 |
| JP | 2000506056 | 5/2000 |
| JP | 2002537895 | 11/2002 |
| JP | 03-508135 | 3/2003 |
| JP | 2007500070 | 1/2007 |
| WO | WO93/05731 A1 | 4/1993 |
| WO | WO 96/26690 A1 | 9/1996 |
| WO | WO 98/08549 A1 | 3/1998 |
| WO | WO 98/48715 A1 | 11/1998 |
| WO | WO 99/17691 A1 | 4/1999 |
| WO | WO 99/21513 A1 | 5/1999 |
| WO | WO 99/30645 A2 | 6/1999 |
| WO | WO 00/38594 A1 | 7/2000 |
| WO | WO 03/041616 A1 | 5/2003 |
| WO | WO 03/061518 A2 | 7/2003 |
| WO | WO 03/101341 A2 | 12/2003 |
| WO | WO 2005/020792 A2 | 3/2005 |
| WO | WO 2006/029316 A1 | 4/2006 |
| WO | WO 2006/060363 A2 | 6/2006 |
| WO | WO 2007/101016 A2 | 9/2007 |
| WO | WO 2007/132332 A2 | 11/2007 |

OTHER PUBLICATIONS

Alio, J. J., et al., "Intracorneal Inlay Complicated by Intrastomal Epithelial Opacification," Arch Ophthalmol, Oct. 2004; vol. 122; 6 pages.

Cheng, et al.; "Predicting subjective judgment of best focus with objective image quality metrics"; Journal of Vision; Apr. 23, 2004; vol. 4(4); pp. 310-321.

Churms, P.W., "The Theory and Computation of Optical Modifications to the Cornea in Refractive Keratoplasty," American Journal of Optometry & Physiological Optics, 56:2, pp. 67-74, Feb. 1979.

Huang et al.; Mathematical Model of Corneal Surface Smoothing After Laser Refractive Surgery; American Journal of Ophthalmology; Mar. 2003; pp. 267-278.

Lang, A.J. et al., "First order design of intracorneal inlays: dependence on keratometric flap and corneal properties," ARVP Abstracts 2006, poster No. 3591, May 3, 2006.

Liou, H. L. et al., "Anatomically accurate, finite model eye for optical modeling", Journal of the Optical Society of America, vol. 14, No. 8, Aug. 1997.

Marsack, et al.; "Metrics of optical quality derived from wave aberrations predict visual performance"; Journal of Vision; Apr. 23, 2004; vol. 4(4); pp. 322-328.

Navarro et al.; Accommodation-dependent model of the human eye with aspherics; J. Opt. Soc Am. A; vol. 2; No. 8; Aug. 1985; pp. 1273-1281.

Watsky, M.A. et al., "Predicting Refractive Alterations with Hydrogel Keratophakia," Investigative Opthalmology & Visual Science, Feb. 1985; vol. 26, pp. 240-243.

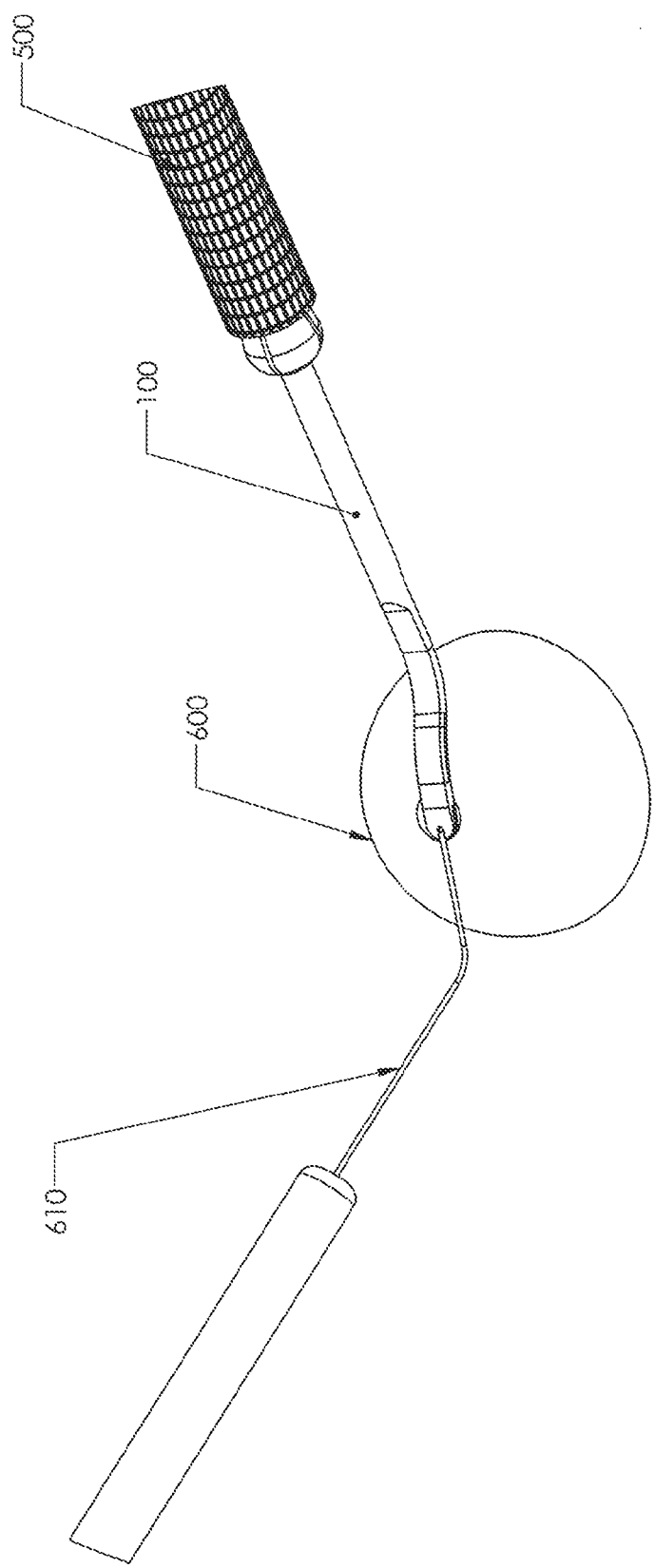

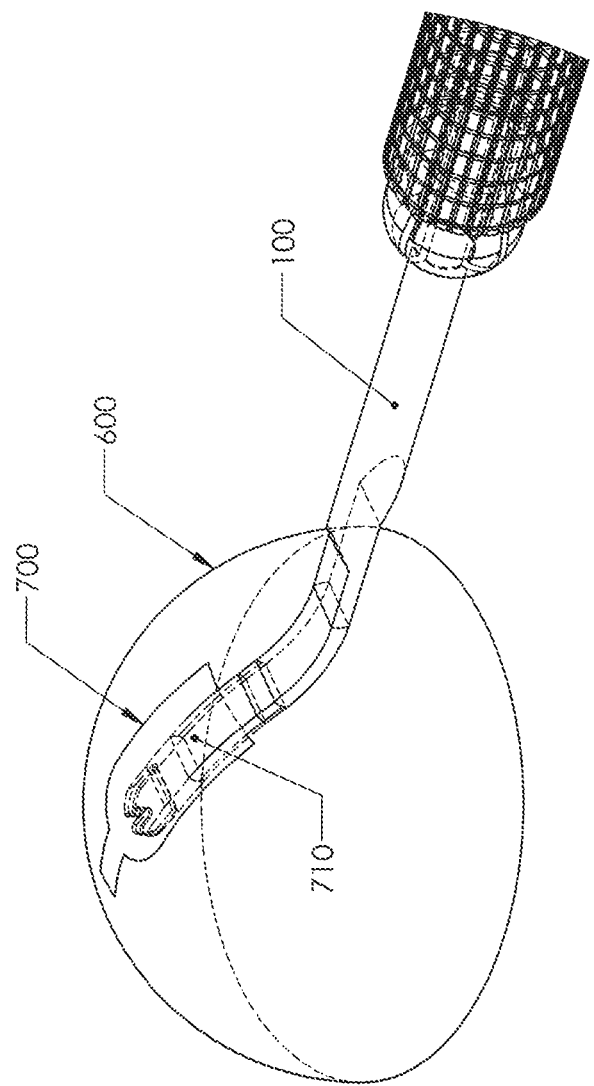

INSERTION SYSTEM FOR CORNEAL IMPLANTS

CROSS REFERENCE TO RELATED APPLICATIONS

This application is a continuation application of pending U.S. application Ser. No. 11/692,835 filed Mar. 28, 2007, the complete disclosure of which is incorporated by reference herein.

FIELD

The field of the invention relates generally to corneal implants, and more particular, to insertion systems for corneal implants.

BACKGROUND

As is well known, abnormalities in the human eye can lead to vision impairment. Some typical abnormalities include variations in the shape of the eye, which can lead to myopia (near-sightedness), hyperopia (far-sightedness) and astigmatism as well as variations in the tissue present throughout the eye, such as a reduction in the elasticity of the lens, which can lead to presbyopia. A variety of technologies have been developed to try and address these abnormalities, including corneal implants.

Corneal implants can correct vision impairment by altering the shape of the cornea. Corneal implants can be classified as an onlay or an inlay. An onlay is an implant that is placed over the cornea such that the outer layer of the cornea, e.g., the epithelium, can grow over and encompass the implant. An inlay is an implant that is surgically implanted into the cornea beneath a portion of the corneal tissue by, for example, cutting a flap in the cornea and inserting the inlay beneath the flap. Both inlays and outlays can alter the refractive power of the cornea by changing the shape of the anterior cornea, by having a different index of refraction than the cornea, or both. Since the cornea is the strongest refracting optical element in the human ocular system, altering the cornea's anterior surface is a particularly useful method for correcting vision impairments caused by refractive errors.

There is a need for improved apparatuses, systems and methods for storing a corneal implant prior to use and for retrieving the corneal implant from storage during a surgical procedure. There is also a need for improved apparatuses, systems and methods for delivering a corneal implant to the cornea and for precisely depositing the corneal implant at a desired location in or on the cornea without damaging the corneal implant.

SUMMARY

Provided herein are apparatuses, systems and methods for storing and retrieving a corneal implant and for delivering the corneal implant in or on the cornea.

In an embodiment, an insertion system comprises an inserter for delivering a corneal implant to a desired location in or on the cornea. The inserter comprises an elongated body having a distal end and a proximal end. The elongated body has a holding space at its distal end for holding the corneal implant to be delivered. The holding space is formed between a top distal portion and a bottom distal portion of the elongated body. In a preferred embodiment, a solution, e.g., saline, substantially fills the holding space with the corneal implant to keep the implant hydrated and to hold the implant in the holding space by the surface tension of the solution. The elongated body of the inserter may also have a curved portion that follows the curvature of the cornea and a clearance bend that provides clearance between the inserter and a facial feature, e.g., nose, of the patient.

In an embodiment, the corneal implant is preloaded in the holding space of the inserter and the preloaded inserter is stored in a storage container filled with storage fluid, e.g., saline, until use. In one embodiment, a cap is placed on the distal end of the inserter after the implant is preloaded. The cap encloses the holding space of the inserter to prevent the corneal implant from moving out of the holding space in the storage fluid during storage. By preloading the implant in the inserter, the surgeon does not have to separately retrieve the implant and place the implant in the inserter, which is difficult due to the small size and delicate nature of the implant.

A method of delivering a corneal implant according to an embodiment includes positioning an inserter with the corneal implant at a desired location in or on the cornea. At the desired location, the corneal implant is held down in the holding space of the inserter by a surgical tool, e.g., cannula. The surgical tool accesses the implant in the holding space through a slot in the inserter. While the corneal implant is held down by the surgical tool, the inserter is retracted to release the corneal implant from the inserter and deposit the corneal implant at the desired location. By holding down the implant at the desired location and retracting the inserter to release the implant, the surgeon is able to precisely deposit the implant at the desired location.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims. It is also intended that the invention not be limited to the details of the example embodiments.

BRIEF DESCRIPTION OF THE FIGURES

FIG. 5A shows the inserter depositing a corneal implant on the cornea according to an embodiment of the present invention.

FIG. 5D shows the inserter depositing a corneal implant within a pocket formed in the cornea according to an embodiment of the present invention.

DETAILED DESCRIPTION

FIGS. 1-5 show an insertion system according to an embodiment that is particular suited for delivering a corneal implant, e.g., inlay, in or on the cornea. The insertion system is also suited for storing the implant prior to its use. The insertion system includes an inserter 100 having an elongated body, which may be made of titanium, stainless steel, plastic, or other biocompatible material. The inserter 100 comprises a distal portion having generally flat top and bottom surfaces. The distal portion of the inserter 100 includes a clearance bend 104 where the inserter is bent to provide clearance between the inserter and a patient's facial features (e.g., nose, cheeks, etc.) as explained further below. The distal portion of the inserter 100 also includes a curved portion 103 that is contoured to follow the shape of a patient's cornea as explained further below. The curved portion 103 is concaved on the bottom surface of the inserter 100.

Figure 4:
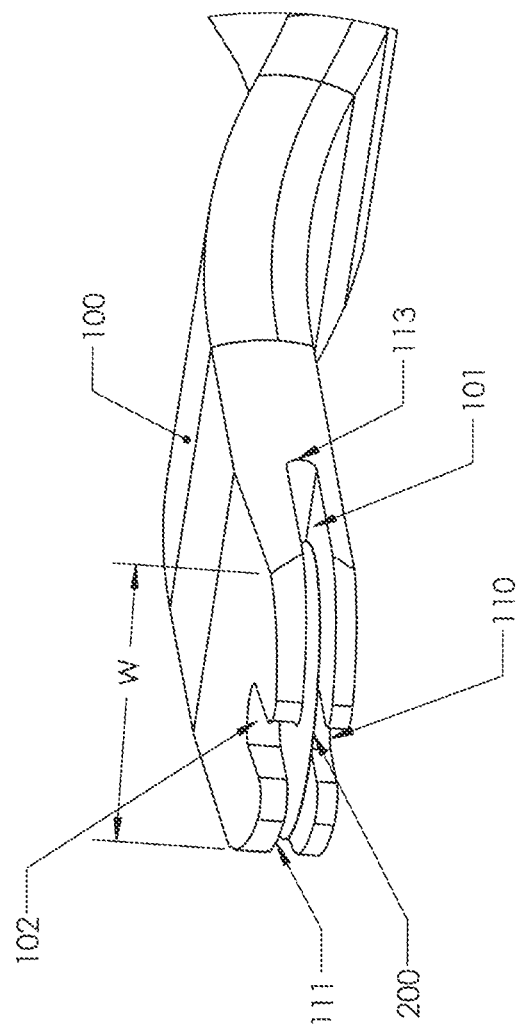
FIG. 4 shows a close-up perspective view of the distal end of the inserter according to an embodiment of the present invention.

The inserter 100 further includes a holding space 101 for holding a corneal implant 200 to be delivered by the inserter. Preferably, saline, BSS or other solution (not shown) is placed in the holding space 101 to hold the implant 200 therein due to surface tension of the saline. The saline stays in the holding space 101 due to capillary forces, thereby keeping the implant hydrated. The inserter also includes top and bottom inserter slots 102 and 110 as shown in FIG. 4. As explained below, the inserter slots 102 and 110 allow a surgeon to view the patient's cornea through the slots for precise placement of the implant 200. In addition, the top inserter slot 102 allows the surgeon to hold down the implant 200 in the holding space 101 at a desired position while the surgeon retracts the inserter 100 to release the implant 200. The surgeon may hold down the implant 200 with a surgical tool, such as a cannula, Sinskey hook or other tool that can fit through the top inserter slot 102. The top inserter slot 102 extends to the leading edge 111 of the inserter 100 so that the tool can hold down the implant 200 as the inserter 100 is retracted. The leading edge 111 of the inserter is preferably rounded to prevent damage to the cornea.

Figure 3:
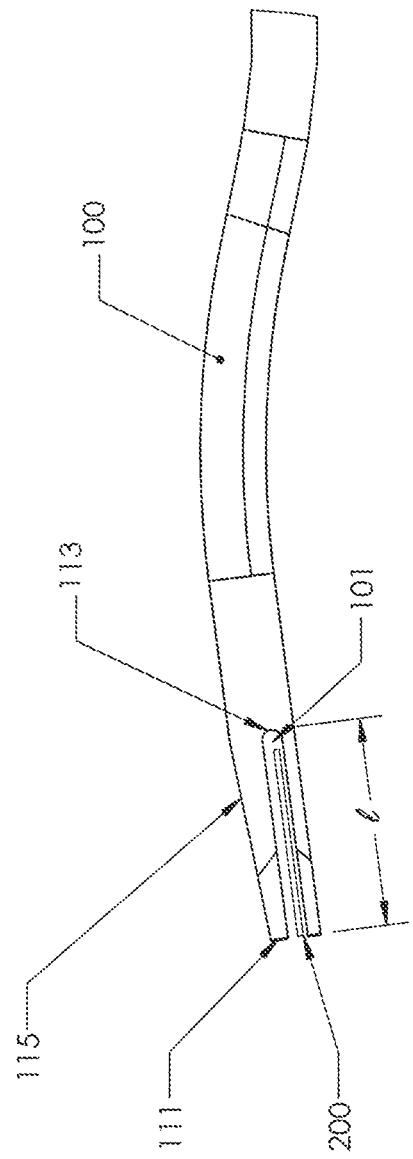
FIG. 3 shows a side view of the distal end of the inserter according to an embodiment of the present invention.

In the preferred embodiment, the width "w" of the holding space 101 is slightly larger than the diameter of the implant 200 to be delivered by the inserter 100 as shown in FIG. 3. In an exemplary embodiment, the implant 200 has a diameter of about 1.5 mm and the width "w" of the holding space 101 is between 1.6 and 1.7 mm. The rounded leading edge 111 of the inserter 100 follows the perimeter of the implant 200. The center length "l" of the holding space 101 is slightly larger than the diameter of the implant 200. As shown in FIG. 3, the center length "l" extends from the center of the leading edge 111 to the back wall 113 of the holding space 101. The geometry of the holding space 101 and the surface tension of the saline in the holding space 101 keep the implant 200 substantially centered in the inserter 100. The height of the holding space 101 may be several times larger than the center thickness of the implant 200 to ensure that enough saline is in the holding space 101 to keep the implant sufficiently hydrated.

The inserter 100 may be manufactured from a rod that is cut and bent to form the inserter 100. In one embodiment, a cylindrical titanium rod is cut and bent to form the inserter 100. In this embodiment, the proximal portion of the inserter 100 is generally cylindrical with angled portions that taper down to the distal portion of the inserter 100.

Figure 1:
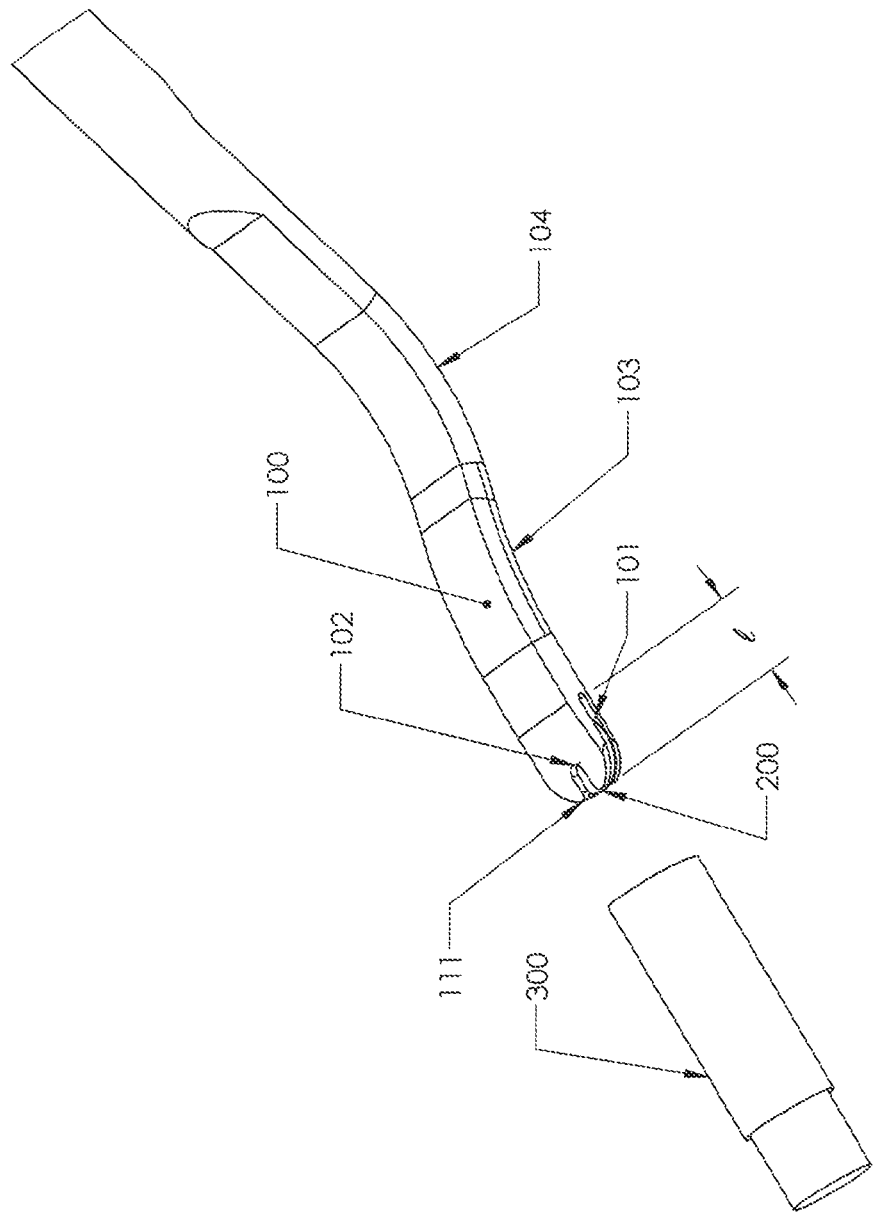
FIG. 1 shows a perspective view of an insertion system comprising an inserter and a cap according to an embodiment of the present invention.
Figure 2:
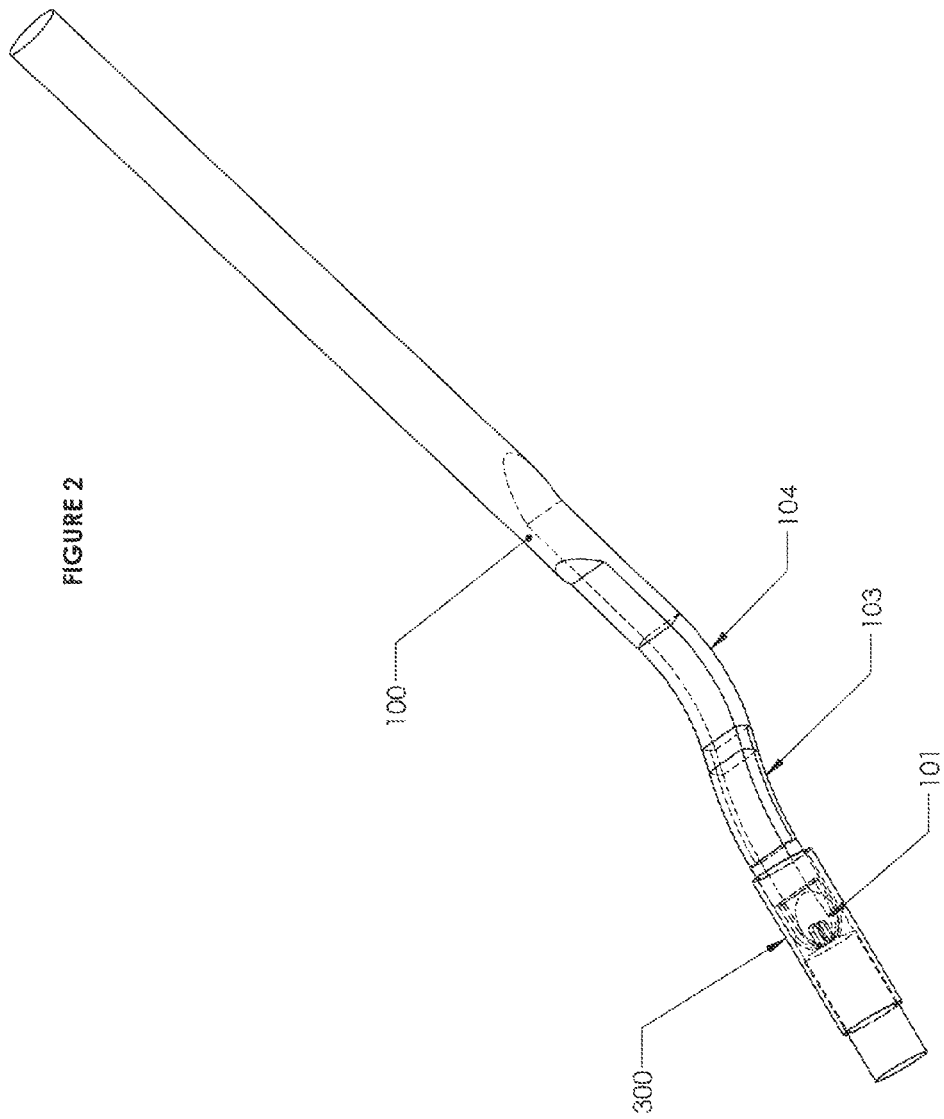
FIG. 2 shows a perspective view of the cap placed on the inserter according to an embodiment of the present invention.

The inserter system further includes an inserter cap 300, which may be made of Teflon (PTFE). In an embodiment, the inserter cap 300 is generally cylindrical and can be fitted snugly on the distal end of the inserter 100 by engaging the sides of the inserter 100 as shown in FIG. 2.

Figure 6:
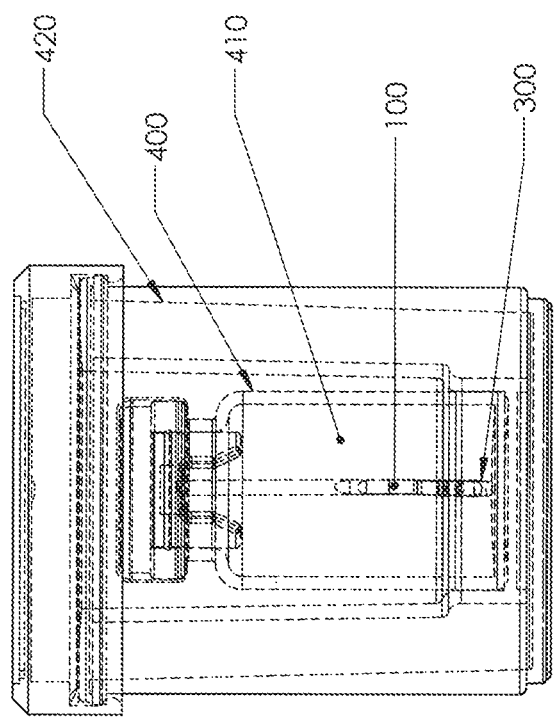
FIG. 6 shows the inserter and cap stored in a container filled with storage fluid according to an embodiment of the present invention.

In a preferred embodiment, the implant 200 is preloaded in the inserter 100 and packaged for later use by the surgeon during an implantation procedure. In this embodiment, the implant is 200 preloaded into the holding space 101 of the inserter 100 with the top surface of the implant 200 orientated to face the top surface of the inserter 100. The implant 200 may be preloaded by submerging both the implant 200 and the holding space 101 of the inserter 100 in a solution, e.g., saline, and inserting the implant 200 into the holding space 101 while they are both submerged. After the implant 200 is preloaded in the inserter 100, the inserter cap 300 is placed on the distal end of the inserter 100. The cap 300 may be placed on the inserter 100 while the holding space 101 is still submerged in the solution. The preloaded inserter 100 assembled with the inserter cap 300 is placed into a vial 400 or other storage container filled with saline 410 or other suitable solution as shown in FIG. 6. The inserter cap 300 prevents the implant 200 from moving out of the inserter 100 when placed in the vial 400 filled with saline 410. The vial 400 is capped and placed in an outer package 420, which is sterilized to store the insertion system until use.

An implantation procedure using an insertion system according to an embodiment will now be given. In this embodiment, the preloaded inserter 100 is removed from the outer package 420 and the vial 400 filled with saline 410. The saline within the space between the inserter cap 300 and the inserter 101 is then removed by placing a sterile surgical sponge (not shown) or other absorbent material on the open end on the inserter cap 300. The sponge draws out the saline from the interior of the cap 300 by capillary action through the opening between the cap 300 and the inserter 101. In the embodiment in which the cap 300 has a generally cylindrical shape, the opening is formed between the cylindrical cap 300 and the flat top and bottom surfaces of the inserter 100. The saline is removed from the spaced between the cap 300 and the inserter 100 while the cap 300 is still on the inserter 100. This is done to prevent the cap 300 from pulling the implant 200 out of the inserter 100 by capillary action when the cap 300 is removed from the inserter 100. After the saline is removed, the cap 300 is removed from the inserter 100. At this point, a small amount of saline or BSS may be applied to the holding space 101 of the inserter 100 to keep the implant 200 hydrated. The saline stays in the holding space 101 due to capillary forces, thereby keeping the implant 200 hydrated during the procedure. Further, the surface tension of the saline holds the implant 200 in the holding space 101 of the inserter 100 so that the implant 200 does not fall out of the inserter 100 during the procedure. This surface tension and the geometry of the holding space 101 keep the implant 200 centered in the inserter 100. To enable a surgeon to better hold the inserter 100, a handle 500 may be attached to the proximal end of the inserter 100 as shown in FIG. 5A. The handle may be similar to handles that attach to disposable blades. Further, the surgeon may determine the proper orientation of the implant based on features of the inserter 100. For example, when the top of the inserter 100, and hence the implant 200, are facing upward, the concaved bottom surface of the curved portion 103 of the inserter 100 is facing downward.

Figure 5B:
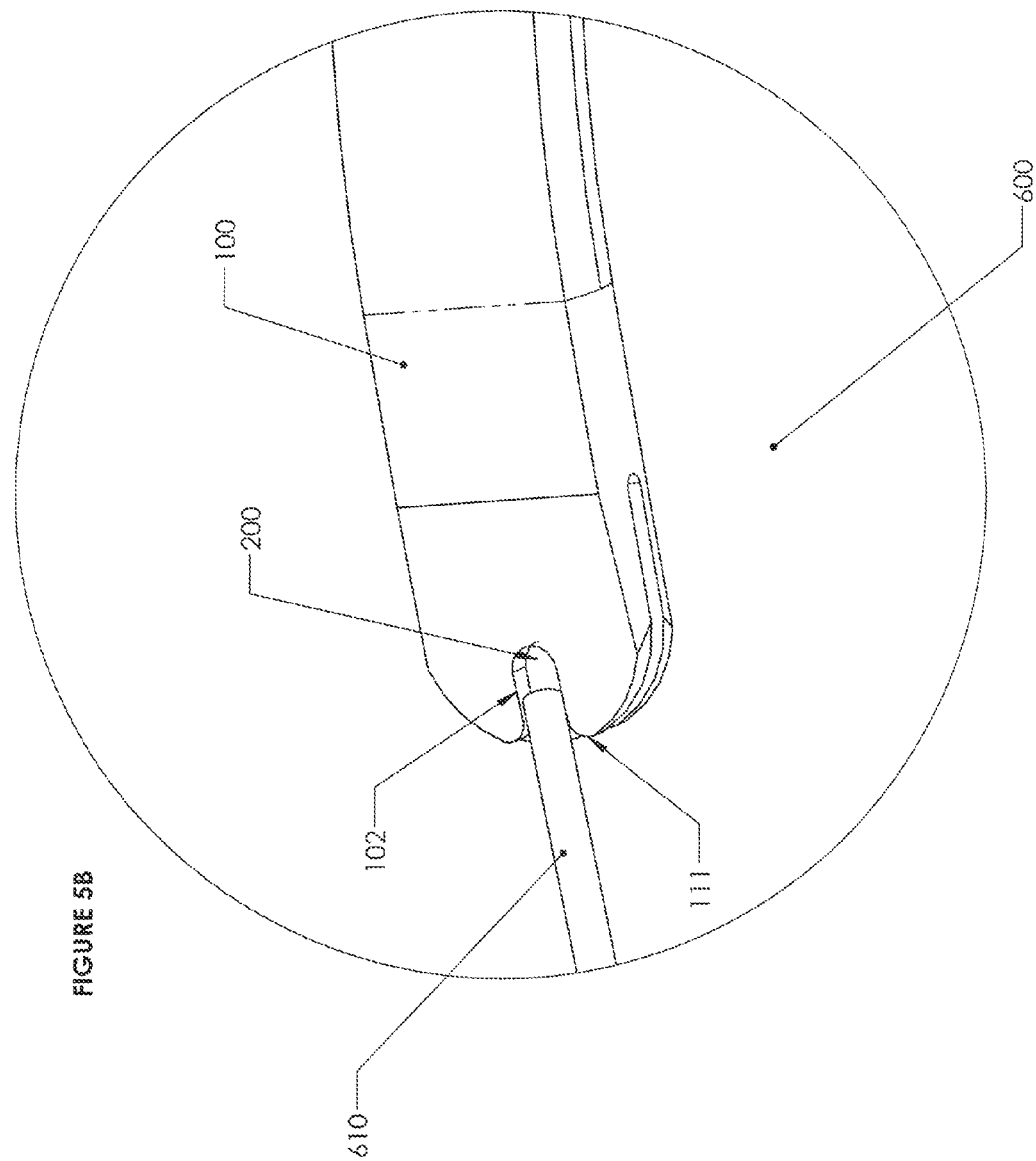
FIG. 5B shows a close-up of the inserter depositing the corneal implant on the cornea.
Figure 5C:
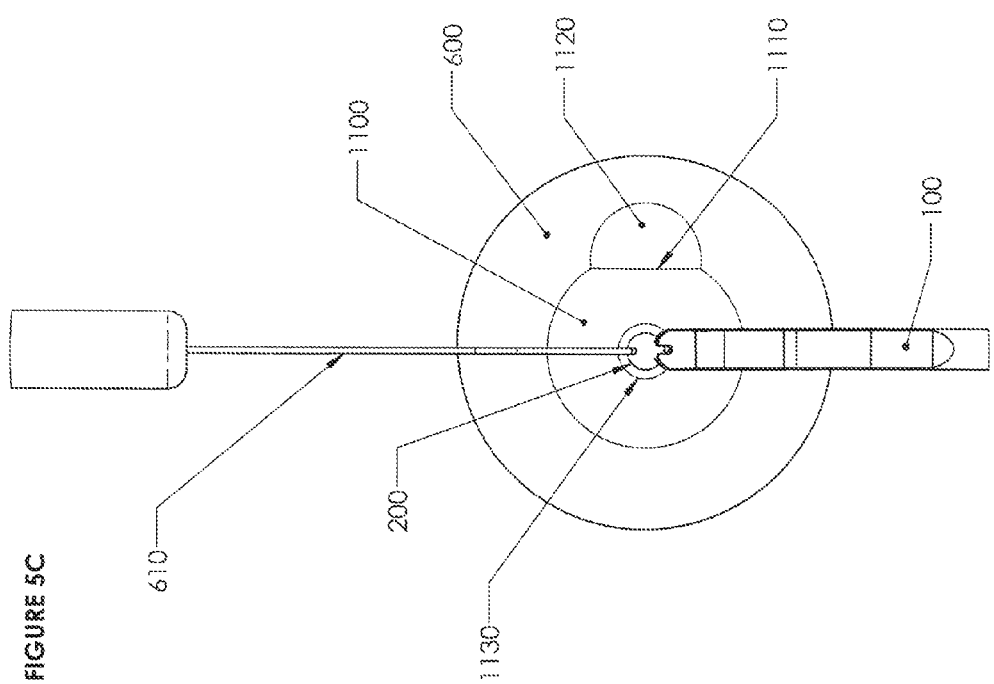
FIG. 5C shows the inserter depositing a corneal implant on an interior surface of the cornea exposed by forming a flap in the cornea according to an embodiment of the invention.

The surgeon may then implant the corneal implant 200 in the patient's cornea. To access the interior of the cornea, a flap may be cut into the cornea and lifted to expose the cornea's interior, e.g., stroma bed of the cornea. An example of this is shown in FIG. 5C, in which a flap 1120 is cut into the cornea 600 and pulled backed to expose the stroma bed 1100 of the cornea. The flap 1120 is attached to the cornea 600 by a flap hinge 1110. The flap 1120 may be cut using a laser, e.g., femtosecond laser, a mechanical keratome or manually. Several methods for forming flaps in corneal tissue, and other related information, are described in further detail in co-pending U.S. patent application Ser. No. 10/924,152, filed Aug. 23, 2004, entitled "Method for Keratophakia Surgery," which is fully incorporated by reference herein. Once the interior is exposed, the surgeon positions the inserter 100 so that implant 200 is at the desired location on the cornea 600, e.g., the patient's pupil or visual axis as shown in FIG. 5A. Prior to positioning the inserter 100, the surgeon may use a surgical sponge to remove excess fluid on the outer surface of the inserter 100 being careful not to remove the saline from the holding space 101. The clearance bend 104 allows the inserter to clear the patient's facial features (e.g., nose) as the surgeon manipulates the inserter 100. To precisely position the implant 200 the surgeon may view the cornea 600 through the inserter slots 102 and 110 and the implant 200, which is transparent. When the implant 200 is at the desired location, the surgeon holds down the implant 200 on the cornea 600 using a surgical cannula, Sinskey Hook or other tool 610 such that implant 200 gently touches the stroma bed of the cornea 600 through the bottom slot 110. This tool 610 holds down the implant 200 through the top inserter slot 102 as shown in FIG. 5B. The surgeon then retracts the inserter 100 from the cornea 600 to release the implant 200 from the inserter 100 and deposit the implant 200 at the desired location. If the implant 200 is not precisely at the desired location, then the surgeon may gently move the implant 200 into position using a surgical sponge, rounded-tip tool, or other tool. In the example shown in FIG. 5C, the implant 200 is centered on the patient's pupil 1130. After the implant 200 is correctly positioned, the surgeon places the flap 1120 over the implant 200.

The implant 200 may be implanted concurrent with a LASIK procedure or post-LASIK. Since a flap is cut into the cornea during a LASIK procedure, the same flap may be used to implant the implant 200. If the implant 200 is implanted post-LASIK, then the LASIK flap may be re-opened or the inserter 100 may be advanced between the flap and the underlying corneal tissue to the desired position. In this example, the LASIK procedure may be used to correct distance vision while the implant is used to provide near vision. Additional details can be found, for example, in U.S. patent application Ser. No. 11/554,544, entitled "Small Diameter Inlays," filed on Oct. 30, 2006, the specification of which is incorporated herein by reference.

The implant 200 may also be implanted through a closed flap instead of an open flap. In this embodiment, the distal portion of the inserter 100 may be inserted between the flap and the underlying corneal tissue and advanced between the flap and underlying corneal tissue to the desired position in the cornea. The distal portion of the inserter 100 preferably has a thin cross-section so that the inserter 100 does not induce corneal wound stretching. The curved portion 103 of the inserter 100 follows the curvature of the cornea allowing the inserter to more easily move between the flap and underlying corneal tissue while minimizing stress on the cornea. Further, the top surface of the inserter 100 preferably a downward slopping portion 115 that slopes downward to the leading edge 111 of the inserter 100 as shown in FIG. 3. In this embodiment, a surgical cannula or other tool may also be inserted between the flap and the underlying corneal tissue to hold down the implant 200 at the desired location and release the implant 200 from the inserter 100.

The implant 200 may also be implanted using different methods to access the interior of the cornea. For example, the interior of the cornea may be accessed through a lamellar pocket, channel, or pathway cut into the cornea. Additional details may be found, for example, in U.S. patent application Ser. No. 11/421,597, entitled "Ocular Tissue Separation Areas With Barrier Regions For Inlays Or Other Refractive Procedures," filed on Jun. 1, 2006, the specification of which is incorporated herein by reference. Methods for creating pockets in the cornea are described in United States Patent Application Publication No. 2003/0014042, published Jan. 16, 2003, entitled "Method of Creating Stromal Pockets for Corneal Implants," which is also fully incorporated by reference herein. For example, the inserter may be inserted into a channel or pocket cut into the cornea and advanced through the channel to position the implant at the desired location in the cornea. A second channel may also be cut into the cornea to provide access for the surgical cannula or other tool used to hold down the implant at the desired location. A pocket is a recess formed within the corneal tissue for receiving the corneal implant and may be accessed through a channel formed in the cornea. FIG. 5D shows an example of the inserter 100 placing the implant 200 within a pocket 700 in formed in the cornea 600 through an opening 710.

Figure 7:
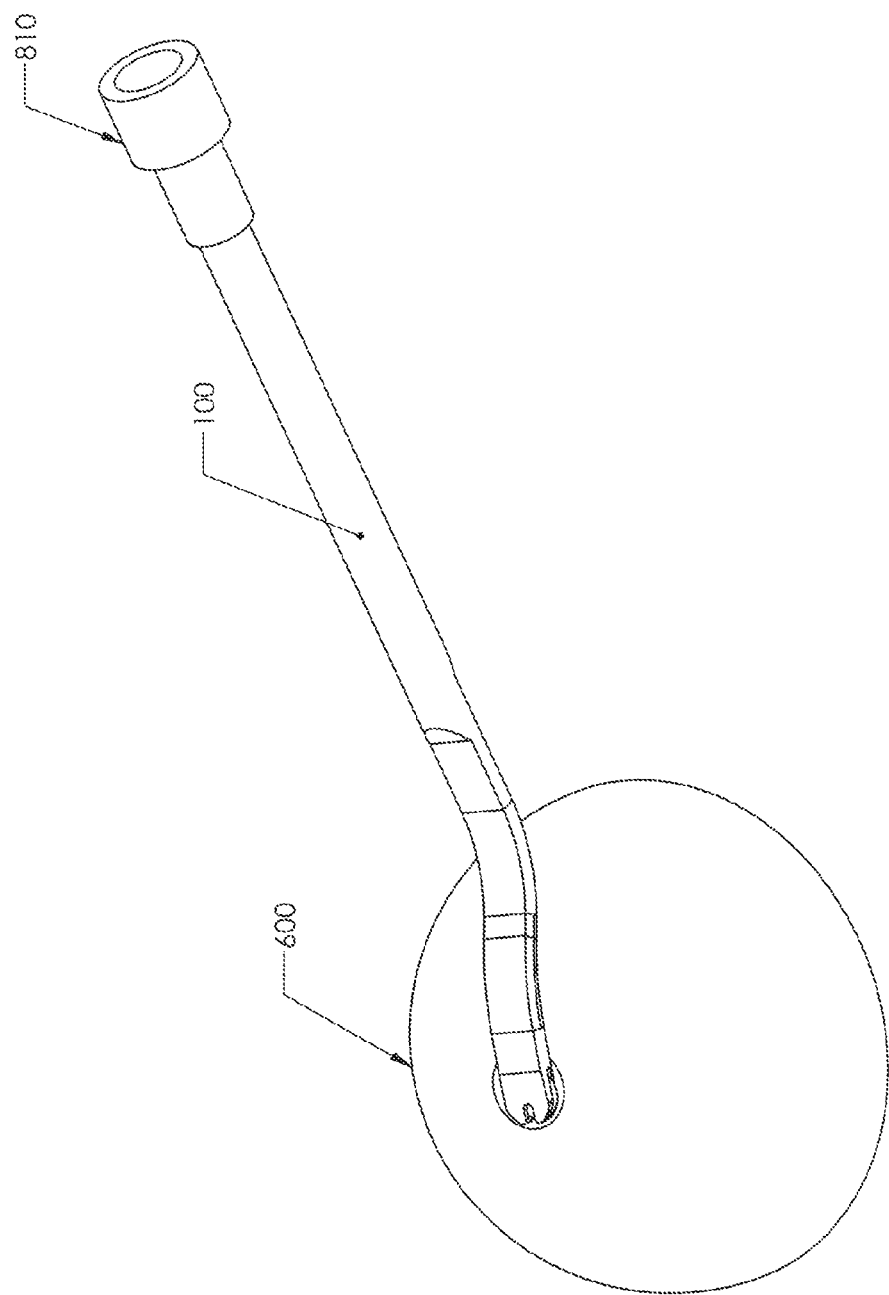
FIG. 7 shows a perspective view of the inserter with a luer lock attached to the proximal end of the inserter according to an embodiment of the present invention.
Figure 8:
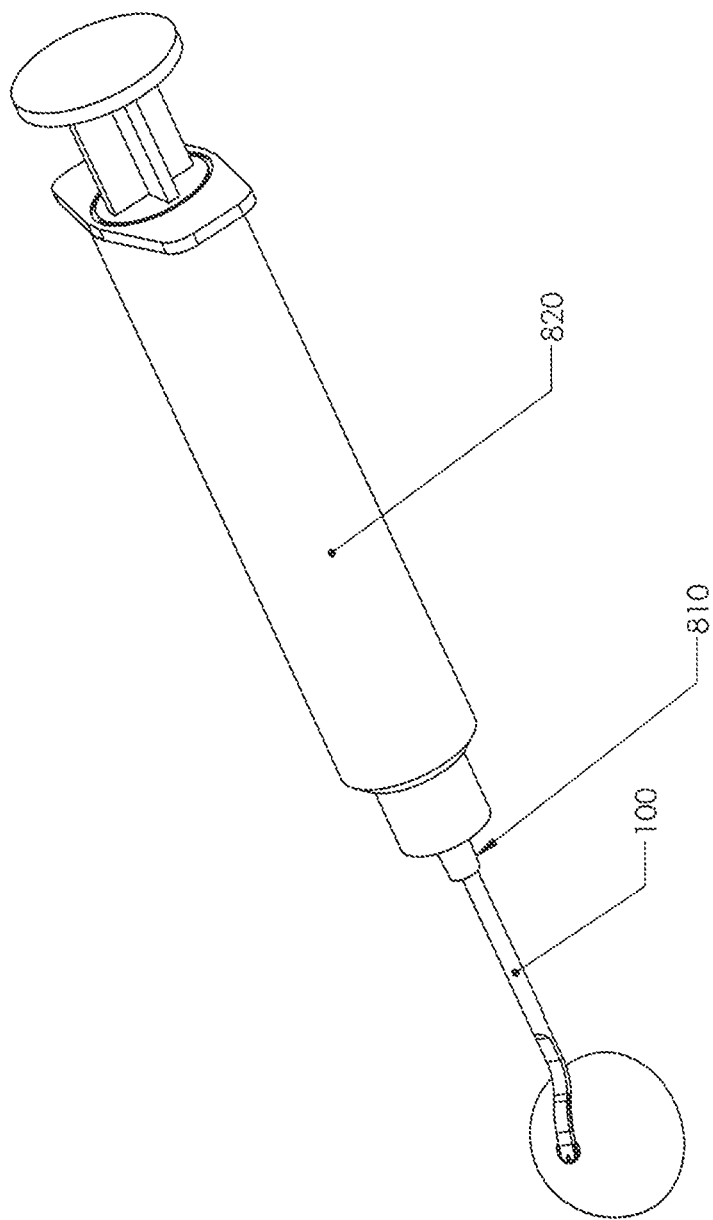
FIG. 8 shows a perspective view of the inserter with a syringe connected to the proximal end of the inserter according to an embodiment of the present invention.

In another embodiment, the inserter 100 may include a channel running through the inserter 100 and extending from the proximal end of the inserter 100 to the holding space 101. The proximal end of the inserter 100 may be connected to a syringe filled with fluid, e.g., saline, for delivering fluid to the holding space 101 through the channel. In this embodiment, the channel may deliver fluid at the back of the holding space 101. This allows a surgeon to deliver a small amount of fluid into the holding space 101 to hydrate the implant 200 and/or gently push the implant 200 out of the holding space 101 for releasing the implant 200 from the inserter 100. For example, when the implant 200 is at the desired location on the cornea, the surgeon may deliver fluid through the channel to help release the implant 200 from the inserter 101. This may be done instead of or in conjunction with the tool used to hold down the implant 200. FIG. 7 shows an inserter 100 according one embodiment comprising a luer lock 810 at the proximal end of the inserter 100 that is configured to mate with a corresponding luer lock of a syringe or other fluid delivering device. FIG. 8 shows an embodiment in which a syringe 820 is connected to the proximal end of the inserter 100 via the luer lock 810 for delivering fluid through the channel.

Figure 9:
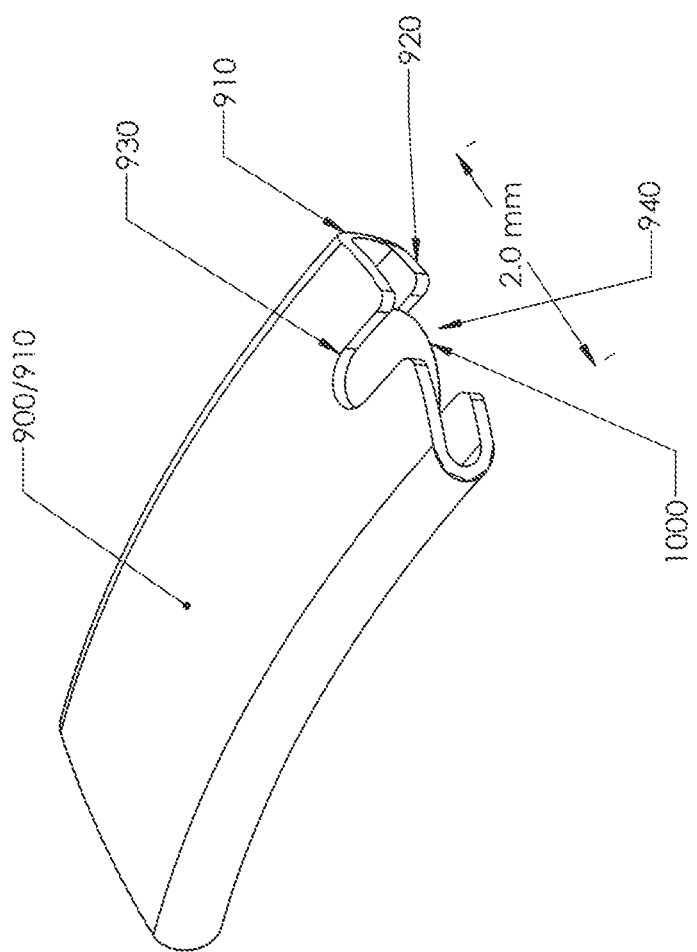
FIG. 9 shows a perspective view of an inserter according to another embodiment of the present invention.
Figure 10:
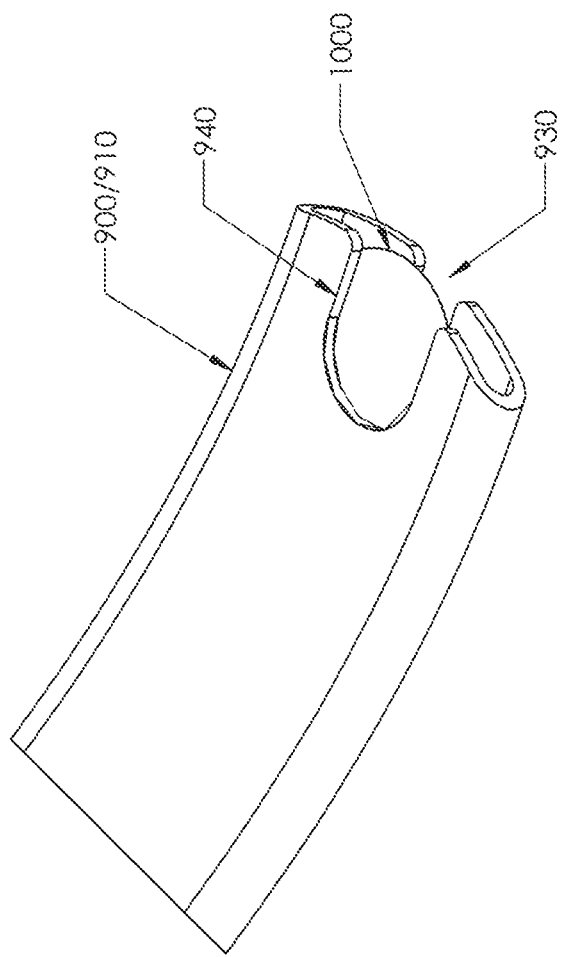
FIG. 10 shows a back view of the distal end of the inserter according to an embodiment of the present invention.

FIGS. 9 and 10 show a distal portion of an inserter 900 according to another embodiment. In this embodiment, the inserter 900 comprises a cannula 910 or tube configured to hold the implant 1000 therein for delivery to the cornea. The cannula 910 preferably has a width slightly larger than the width of the implant 1000 to be delivered by the inserter 900. The cannula 910 also preferably has a height that is slightly larger than the thickness of the implant 1000. The distal end 920 of the cannula 910 is preferably shaped to hold the implant 1000 in an unstressed state. The cannula 910 may be slightly curved along its width and/or length to follow the curvature of the cornea. Fluid, e.g., saline or BSS, may be delivered to the implant 1000 through a channel in the inserter 900 to ensure that the implant 1000 is hydrated prior to use and/or to release the implant 1000 from the inserter 900.

Figure 11:
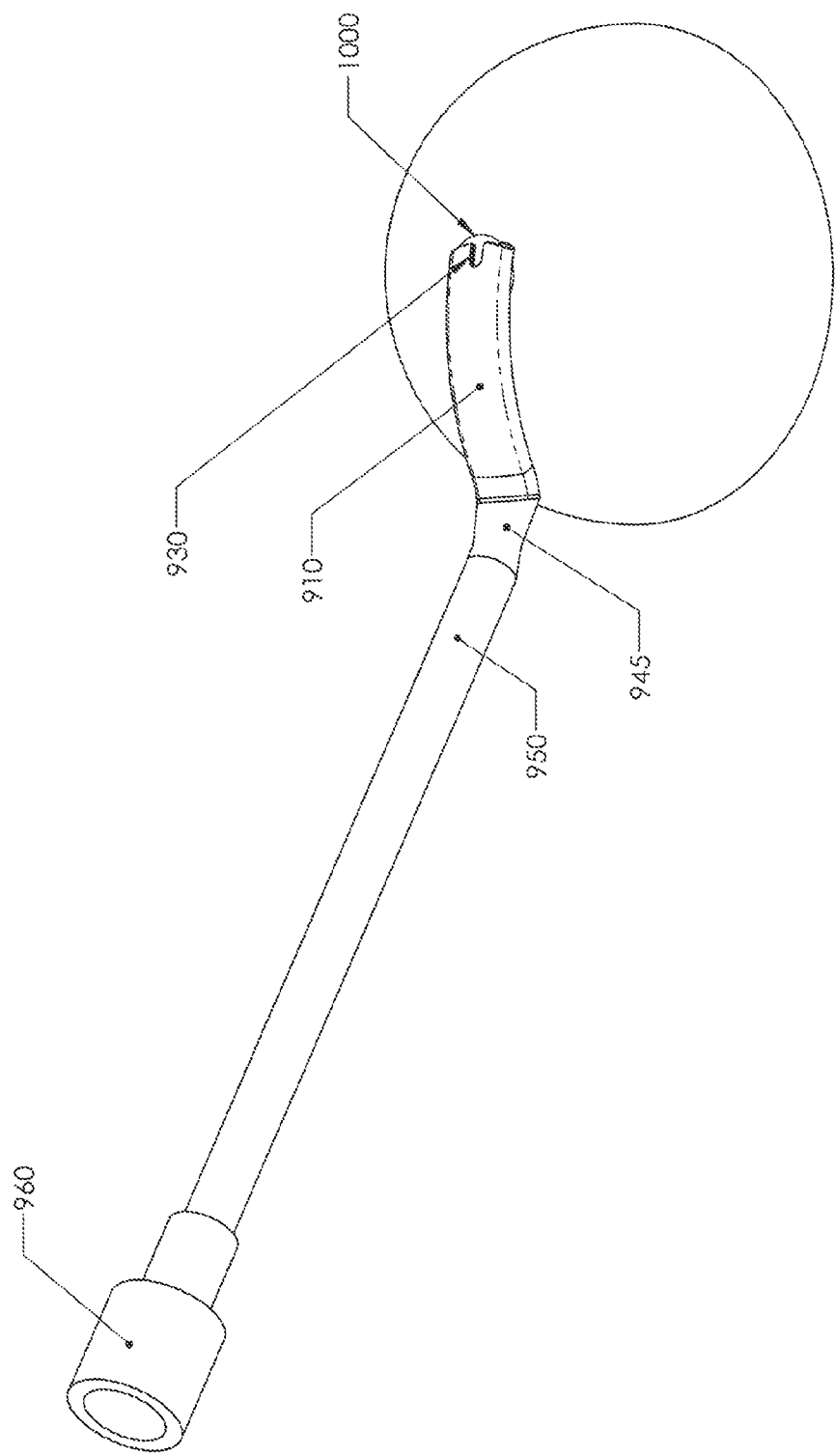
FIG. 11 shows the inserter depositing a corneal implant on the cornea according to an embodiment of the present invention.

The inserter 900 also includes a top inserter slot 930 through which a surgical cannula, Sinskey Hook or other tool can be used to hold down the implant 1000 at the desired location in the cornea. The inserter 900 also includes a bottom opening 940 through which the implant 1000 can contact the cornea when the implant is held down as shown in FIG. 10. Preferably, the edges and corners at the tip of the cannula 910 are smooth and rounded to prevent cutting by the cannula 910 and damage to the cornea or implant from the tip of the cannula. A handle may be attached to the proximal end of the inserter for easier handling by the surgeon. Further, a syringe or other fluid delivering device may be connected to the inserter 900 for delivering fluid to the implant through the channel in the inserter 900. FIG. 11 shows the entire inserter 910, which includes a clearance bend 945 and an elongated portion 950 with an optional luer lock 960 at the proximal end of the inserter 910 for connecting, e.g., a fluid delivering device to the inserter 910.

The implant 1000 may be implanted in the cornea using procedures similar to the ones discussed above. For example, a flap may be cut into the cornea and lifted to expose a stroma bed of the cornea. The surgeon may then position the implant 1000 at the desired location using the inserter 900. When the implant 1000 is at the desired position, the surgeon may use a surgical cannula or other tool to hold the implant 1000 through the top inserter slot 930. The surgeon may hold down the implant 1000 such that the bottom surface of the implant 1000 contacts the cornea through the bottom opening 940 of the inserter 900. While the implant 1000 is held down at the desired location, the surgeon retracts the inserter 900 to deposit the implant 1000 on the cornea. The surgeon may also deliver fluid to the implant 1000 through the channel in the inserter to release the implant 1000 from the inserter 900. After the implant 1000 is correctly positioned, the surgeon places the flap over the implant 1000. FIG. 11 shows an example of the inserter 900 positioned over the desired location of the cornea for depositing the implant 1000 at the desired location.

The implant 1000 may also be implanted using other procedures including implantation through a channel, pocket or pathway cut into the cornea for access to the desired position in the cornea. In these procedures, the inserter 900 may be moved to the desired position through the channel, pocket or pathway. The thin cross section of the inserter 900 minimizes stress on the cornea as the inserter 900 is advanced through the channel, pocket or pathway. A second channel may also be cut into the cornea to provide access for the surgical tool used to hold down the implant 1000 at the desired location.

The inserter systems described herein may be used to implant various types of corneal implant. For example, the inserter systems may be used to implant corneal implants deep within the cornea such as intraocular lenses or at lower depths such as inlays. The inserter systems may also be used to place an onlay on the surface of the cornea. Thus, the inserter systems may be used to implant corneal implants of various rigidity, sizes and properties at various depths in the cornea. The corneal implant may be an inlay, lens, or the like.

In the foregoing specification, the invention has been described with reference to specific embodiments thereof. It will, however, be evident that various modifications and changes may be made thereto without departing from the broader spirit and scope of the invention. As another example, each feature of one embodiment can be mixed and matched with other features shown in other embodiments. As yet another example, the order of steps of method embodiments may be changed. Features and processes known to those of ordinary skill may similarly be incorporated as desired. Additionally and obviously, features may be added or subtracted as desired. Accordingly, the invention is not to be restricted except in light of the attached claims and their equivalents.

What is claimed is:

1. A method of delivering a corneal implant comprising:
   providing a delivery device with a distal portion, the distal portion including a holding space with a corneal implant retained therein in a substantially unstressed configuration due to surface tension of a fluid in the holding space, wherein the holding space is defined between a top distal portion and a bottom distal portion of the delivery device;
   positioning the distal portion of the delivery device adjacent to corneal tissue; and
   depositing the corneal implant onto the corneal tissue.

2. The method of claim 1, wherein the delivery device further comprises a slot in the top distal portion that extends to a leading edge of the delivery device, the method further comprising:
   applying a force on the corneal implant with a surgical tool positioned within the slot; and
   retracting the delivery device from the cornea to deposit the corneal implant onto the corneal tissue.

3. The method of claim 1, further comprising:
   forming a flap in the cornea;
   lifting the flap to expose a corneal bed; and
   placing the flap over the corneal implant on the corneal bed after the corneal implant is deposited onto the corneal bed.

4. The method of claim 1, further comprising:
   forming a channel in a cornea to the corneal tissue; and
   advancing the distal end of the delivery device through the channel to access the corneal tissue.

5. The method of claim 1, further comprising:
   forming a pocket within the cornea to receive the corneal implant; and
   advancing the distal end of the delivery device to the pocket.

6. The method of claim 1, wherein the fluid comprises saline.

7. A method of securing a corneal implant in a delivery device using surface tension, comprising:
   providing a delivery device with a distal portion, the distal portion including a holding space between a top distal portion and a bottom distal portion of the delivery device;
   positioning a corneal implant and a fluid within the holding space so that the corneal implant is retained within the holding space in a substantially unstressed configuration due to the surface tension of the fluid.

8. The method of claim 7 further comprising
   positioning the distal portion of the delivery device adjacent to corneal tissue; and
   depositing the corneal implant onto the corneal tissue.

9. The method of claim 7, wherein the distal portion further comprises a slot in the top distal portion to provide access to the holding space, the method further comprising:
   positioning a surgical tool in the slot;
   applying a force on the corneal implant with a surgical tool; and
   retracting the delivery device from the cornea to deposit the corneal implant onto the corneal tissue.

10. The method of claim 7, further comprising:
forming a flap in a cornea;
lifting the flap to expose a corneal bed; and
depositing the corneal implant from the holding space onto the corneal bed; and
placing the flap over the corneal implant on the corneal bed.

* * * * *